United States Patent [19]

Kummann

[11] Patent Number: 4,952,305
[45] Date of Patent: Aug. 28, 1990

[54] PROCESS AND APPARATUS FOR THE SEPARATION OF HYDROCARBONS

[75] Inventor: Paul Kummann, Munich, Fed. Rep. of Germany

[73] Assignee: Linde Aktiengesellschaft, Wiesbaden, Fed. Rep. of Germany

[21] Appl. No.: 302,282

[22] Filed: Jan. 27, 1989

[30] Foreign Application Priority Data

Jan. 28, 1988 [DE] Fed. Rep. of Germany ....... 3802553

[51] Int. Cl.⁵ .................................................. F25J 3/02
[52] U.S. Cl. ...................................... 208/340; 62/34; 62/31; 208/355
[58] Field of Search ............... 208/340, 341, 342, 351, 208/355; 62/29, 31, 33, 34, 38, 39

[56] References Cited

U.S. PATENT DOCUMENTS

| | | | |
|---|---|---|---|
| 4,453,956 | 6/1984 | Fabbri et al. ...................... | 62/34 X |
| 4,486,209 | 12/1984 | Fabbri et al. ...................... | 62/18 |
| 4,525,187 | 6/1985 | Woodward et al. ............... | 62/34 X |
| 4,664,687 | 5/1987 | Bauer ................................ | 208/340 X |
| 4,707,171 | 11/1987 | Bauer . | |

Primary Examiner—Glenn Caldarola
Attorney, Agent, or Firm—Millen, White & Zelano

[57] ABSTRACT

In a process for obtaining higher-boiling hydrocarbons from a gaseous stream, the latter is first partially condensed and the thus-formed liquid fraction is introduced into a rectification process whereas the gaseous fraction is scrubbed in a scrubbing column using condense residual gas from the rectification. The thus-formed bottom product is likewise passed on to rectification.

In order to enhance the scrubbing step by condensed gas, higher hydrocarbons are admixed to this residual gas. Thereby, on the one hand, the residual gas is subjected to improved initial condensation and, on the other hand, the scrubbing effect is enhanced.

23 Claims, 3 Drawing Sheets

PROCESS AND APPARATUS FOR THE SEPARATION OF HYDROCARBONS

BACKGROUND OF THE INVENTION

The invention relates to a process and apparatus for the separation of higher-boiling hydrocarbons from a gaseous stream containing the latter and lower-boiling components.

Processes are known wherein the gaseous stream is cooled, partially condensed, and separated into a liquid fraction and a gaseous fraction. The liquid fraction is fractionated by rectification into a product stream containing lower-boiling components. The gaseous fraction separated after partial condensation is conducted to a scrubbing column wherein higher hydrocarbons are scrubbed out.

Such processes serve above all for the separation of higher-boiling hydrocarbons from natural gases or other gases, e.g., refinery waste gases or residual gases from a synthesis process. Since the market prices for $C_3/C_4$ hydrocarbon mixtures have risen, increased efforts have been directed to provide improved processes for the production thereof.

DOS 3,511,636 discloses a process of the type discussed above relating to the separation of $C_{2+}$ or $Cp_{3+}$ hydrocarbons from a gaseous stream containing light hydrocarbons and, in some cases, components boiling lower than methane. The gaseous stream to be fractionated is partially condensed into a gaseous stream essentially free of $C_{2+}$ or $C_{3+}$ hydrocarbons and into a liquid stream containing essentially only $C_{2+}$ or $C_{3+}$ hydrocarbons.

The liquid stream is freed from the remaining lower-boiling components in a rectifying column, together with a further fraction. A high-purity $C_{2+}$ or $C_{3+}$ hydrocarbon fraction is withdrawn from the bottom of the column and can be passed onto further fractionating.

The gaseous stream of the partial condensation is conducted into a scrubbing column in order to remove higher-boiling components that have remained therein. For this purpose the residual gas from the head of the rectifying column is introduced, in partially condensed form, as scrubbing medium into the scrubbing column wherein the higher-boiling components are scrubbed out of the rising gaseous stream. From the bottom of the scrubbing column, a fraction is withdrawn enriched in higher-boiling components and is fed, as the above-mentioned further fraction, into the rectifying column for separation. At the head of the scrubbing column, a gaseous fraction depleted in higher-boiling hydrocarbons is withdrawn.

Although the yield of $C_{2+}$ and $C_{3+}$ hydrocarbons is satisfactory, a valuable amount of higher-boiling components still escapes together with the gaseous fraction from the scrubbing column. In order to increase the yield further, the temperature or the pressure of the scrubbing column could be lowered. However, for this purpose an expansion machine such as a turbine would be required, for example, which represents an expensive part of the apparatus.

Under certain conditions, especially in the case of a high proportion of $CO_2$ in the gaseous stream to be separated, lowering of the temperature of the scrubbing column is disadvantageous. In the event of a high proportion of $CO_2$, lowering the temperature of the scrubbing column can lead to $CO_2$ freezing out as a solid. This would adversely affect the course of the process.

Therefore, losses in yield had to be tolerated heretofore in the conductance of the above-mentioned process, if the $CO_2$ should not, or could not be removed from the gaseous stream by expensive preliminary purification steps.

SUMMARY OF THE INVENTION

An object of the present invention is to develop a process and apparatus of the type discussed above wherein an increase in the yield of higher-boiling hydrocarbons is attained in a simple and economical fashion, even with a high proportion of $CO_2$ in gaseous stream to be separated.

Upon further study of the specification and appended claims, further objects and advantages of this invention will become apparent to those skilled in the art.

These objects are attained by admixing with a residual gas of the rectification, which is to be used as scrubbing medium in the scrubbing column, liquid $C_{3+}$, $C_{4+}$ or $C_{5+}$ hydrocarbons.

It has been found within the scope of the invention that, by admixing $C_{3+}$ hydrocarbons and mixtures of higher-boiling hydrocarbons to the residual gas used as scrubbing medium, an increase in the yield of higher-boiling hydrocarbons, especially $C_{3+}$ or $C_{4+}$ hydrocarbons, is obtained.

Thus, an embodiment of the process according to the invention comprises:

cooling and partially condensing the crude gaseous stream, and separating the partially condensed gaseous stream into a liquid fraction and a gaseous fraction;

fractionating the liquid fraction by a rectification step into a product stream containing essentially higher-boiling hydrocarbons and into a residual gas stream containing lower-boiling components;

conducting the gaseous fraction separated after partial condensation to a scrubbing column wherein higher-boiling hydrocarbons are scrubbed out of the gaseous fraction using residual gas, obtained in the rectification step, as scrubbing medium, after partial condensation of the residual gas;

delivering a fraction enriched in higher-boiling hydrocarbons obtained from the bottom of the scrubbing column to the rectification step; and adding a liquid stream of $C_{3+}$, $C_{4+}$ or $C_{5+}$ hydrocarbons to the residual gas of the rectification step to provide an admixture used as the scrubbing medium in the scrubbing column.

Primarily, two effects result from the process the course of which has been altered as compared with the state of the art. On the one hand, the residual gas of the rectification experiences an improved initial condensation on account of the addition of higher-boiling boiling hydrocarbons; in other words, the admixture brings about an almost complete condensation of the residual gas. On the other hand, by admixing the liquid $C_{3+}$, $C_{4+}$ or $C_{5+}$ hydrocarbons, a kind of "absorptive scrubbing out" procedure is performed in the scrubbing column.

Thus, in the process according to the invention, generally about 30 to 98 vol % of the residual gas is condensed, preferably 40 to 95 vol %. In comparison, the process of DOS 3,511,636 obtained a condensation of about only 5 to 15 vol % less of the residual gas.

In the process, the residual gas stream, which is to be admixed with a liquid stream of $C_{3+}$, $C_{4+}$ or $C_{5+}$ hydrocarbon, contains a major proportion, e.g., 90 to 99.9 vol %, especially 95 to 99.5 vol %, of lower-boiling components such as, for example, $H_2$, $N_2$, CO, $CO_2$, methane and ethane. However, the residual gas also contains 0.1 to 10 vol %, especially of higher-boiling components such as $C_{3+}$ or $C_{4+}$ hydrocarbons. During subsequent cooling of the residual gas stream, the higher-boiling components condense. The condensate thus formed together with the admixed liquid $C_{3+}$, $C_{4+}$ or $C_{5+}$ hydrocarbon stream is used as the scrubbing medium in the scrubbing column. The use of admixed scrubbing medium is novel.

In the admixing step, the amount of higher-boiling hydrocarbons employed is generally 5 to 20 vol %, preferably 10 to 15 vol % relative to the resultant total amount of the admixture. The liquid fraction resulting from the admixture and condensation of the residual gas generally contains the following components:

| | |
|---|---|
| $C_1$ | 15 to 40 vol % |
| $C_2$ | 30 to 50 vol % |
| $C_3$ | 0.1 to 2 vol % |
| $C_4$ | 0 to 5 vol % |
| $C_5$ | 3 to 15 vol % |
| $C_{6+}$ | 2 to 5 vol % |

The principle of scrubbing, as known from DOS 3,511,636, is based, first of all, on the fact that the partially condensed residual gas of the rectification acts as a coolant. Upon entrance into the scrubbing column, the condensate is revaporized, releasing cold, since it is expanded from the relatively high partial pressure of condensate formation to a lower partial pressure. The cooling effect is increased in the mode of performing the process described herein, because it is possible to condense the residual gas of the rectification in a larger proportion. The resultant cooling action allows the higher-boiling hydrocarbons, that have still remained in the gaseous fraction, to condense.

Superimposed on this principle is the process called "absorptive scrubbing out." The addition of higher boiling components to the residual gas enhances the scrubbing out process.

As explained above, too low a temperature can lead to problems in case of high proportions of $CO_2$ in the gaseous stream to be separated. The course of the process as followed by the present invention makes it possible to raise the temperature of the scrubbing column with a simultaneous improvement in yield. Due to the increased operating temperature of the scrubbing column, components that do not boil as low as 220K, such as, for example, $CO_2$, $CH_4$, $C_{2+}$ hydrocarbons, etc., are dissolved in the liquid fraction of the scrubbing column. In particular, there are no deposits of solids in the liquid fraction fed to the rectification.

The process according to the invention is thus suitable for treating gaseous streams containing up to 20 vol % $CO_2$, preferably up to 15 vol %.

Furthermore, the higher-boiling components are scrubbed out of the gaseous fraction more effectively due to the addition of heavier components.

In a development of the invention, the liquid $C_{3+}$, $C_{4+}$ or $C_{5+}$ hydrocarbons stem from a further fractionation of the product stream from the rectification which contains $C_{3+}$ or $C_{4+}$ hydrocarbons.

The bottom product of the rectifying column is usually separated further so that individual product streams are created. By stepwise rectification, the individual streams are produced:

$$C_{3+}(l) \rightarrow C_3(g) + C_{4+}(l) \rightarrow C_4(g) + C_{5+}(l)$$

(l) = liquid, (g) = gaseous

The separation may be conducted stepwise in a series of rectification columns. Also a single column can be used with $C_3$ top, or LPG top ($C_3/C_4$), or LPG side product and $C_{5+}$ bottom product.

Since, with progressive separation, a pressure drop occurs simultaneously in the individual streams, these streams are suitable raised to the pressure required for admixing before they are admixed to the residual gas of the rectifying column. Admixing of the higher-boiling hydrocarbons with residual gas may also be achieved subsequent to partial condensation of residual gas and subcooling of the higher-boiling hydrocarbon streams.

For the addition to the residual gas, at least a portion of one of the liquid streams provided by further rectification can be employed. According to the invention, the liquid $C_{3+}$, $C_{4+}$ or $C_{5+}$ hydrocarbons are utilized for $C_{3+}$ separation whereas preferably only the liquid $C_{4+}$ or $C_{5+}$ hydrocarbons or at least a portion of these products are employed for $C_{4+}$ separation.

Also, a partial stream of the bottoms liquid stream from rectification can be recycled and employed as the liquid $C_{3+}$, $C_{4+}$ or $C_{5+}$ stream which is admixed with the residual gas stream without further purification or rectification of the partial stream.

In addition, the invention is also directed to an apparatus for performing the process according to the invention, especially an apparatus for performing the scrubbing and rectification steps.

The apparatus for the scrubbing and rectification operations comprises a scrubbing column with inlet means for introducing a gaseous fraction into the lower portion of the scrubbing column, and also inlet means for introducing condensed residual gas from the subsequent rectification step as a scrubbing medium into the head of the scrubbing column. An outlet is provided in the head of the scrubbing column for removal of a residual gaseous fraction. The loaded scrubbing medium is conducted from an outlet in the bottom of the scrubbing column to a heat exchange means wherein it is heated. The heated loaded scrubbing medium is subsequently delivered to a rectification column.

The rectification column is equipped with heat exchange means at the head thereof to provide a reflux stream formed from condensed higher boiling hydrocarbons. An outlet is provided in the bottom of the rectification column for removal of the $C_{3+}$ or $C_{4+}$ product fraction. Outlet means is provided in the head of the rectification column for removal of a residual gas fraction. The residual gas fraction is delivered to an admixing means whereby $C_{3+}$, $C_{4+}$ or $C_{5+}$ hydrocarbons are admixed with the residual gas fraction. The admixture is subsequently cooled in a heat exchange means wherein a portion of the residual gas fraction is condensed. The condensed residual gas fraction is delivered to the inlet means at the head of the scrubbing column, wherein it is used as a scrubbing medium.

In another embodiment of the apparatus according to the invention, the apparatus comprises:

a scrubbing column, the scrubbing column having a first inlet means in a lower portion thereof for introduction of a gaseous fraction and a second inlet means, in an upper portion of the scrubbing column, for delivery of scrubbing medium, the scrubbing column also having a first outlet means in the upper portion thereof for removal of a residual gas stream and a second outlet means in the lower portion thereof for removal of loaded scrubbing medium;

first delivery means connected to the second outlet of the scrubbing column for removing loaded scrubbing medium from the scrubbing column and delivering same to a heat exchanger wherein loaded scrubbing medium is heated;

a rectification column, the rectification column comprising a first inlet means, in fluid communication with the first delivery means, for the introduction of heated, loaded scrubbing medium to the rectification column, a heat exchanger in an upper portion of the rectification column to condense higher-boiling hydrocarbons from a rising gaseous fraction, a product outlet means in a lower portion of the rectification column for removal of a product stream of higher-boiling hydrocarbons, and a gas outlet means in the head of the rectification column for the discharge of a residual gas fraction;

second delivery means, connected to the gas outlet of the rectification column, for delivering a residual gas fraction to a heat exchange means, wherein the residual gas fraction is subject to condensation, and subsequently delivering a condensed residual gas fraction to the second inlet means of the scrubbing column, wherein condensed residual gas fraction is employed as scrubbing medium; and admixture means in fluid communication with the second delivery means at a point upstream of the heat exchange means wherein a liquid stream of higher-boiling hydrocarbons is admixed with residual gas prior to condensation in the heat exchange means.

In a further embodiment of the apparatus according to the invention, a separator is provided upstream of the scrubbing column and rectification column. The crude gas to be separated is initially partially condensed in heat exchange means and then delivered to the separator. A gaseous fraction is removed from the head of the separator via discharge means and delivered to the bottom portion of the scrubbing column. The resultant liquid fraction is removed from the bottom of the separator, heated in a heat exchange means and then delivered to the rectification column. Preferably, the liquid fraction is introduced to the rectification column at a point below that of the introduction point of the loaded scrubbing medium. Prior to being heated, the liquid fraction can be expanded or compressed.

In a further embodiment according to the invention, the separator and scrubbing column are combined into a single integrated unit. In this embodiment, the crude gas is initially cooled in a heat exchange means and then delivered to the bottom of a separator/scrubbing column. The bottom of the separator/scrubbing column is separated or compartmentalized, e.g., by a vertical divider, into two bottom sections. In a first bottom section, the partially condensed crude gas is separated into a liquid fraction and a gaseous fraction. The gaseous fraction rises in the separator/scrubbing column, wherein it is contacted by the admixture of higher-boiling hydrocarbons and condensed residual gas. The resultant loaded scrubbing medium is collected in the second bottom portion of the separator/scrubbing column.

The liquid fraction resulting from separation of the partially condensed crude gas is removed from the first bottom section of the separator/scrubbing column, heated in a heat exchange means and delivered to the rectification column. The loaded scrubbing medium is removed from the second bottom section of the separator/scrubbing column, heated in a heat exchange means and also delivered to the rectification column. Preferably, the heated, loaded scrubbing medium is delivered to the rectification column at a point above that of the introduction point of the heated liquid fraction.

The process generally is applicable to the separation of higher-boiling hydrocarbons from gaseous mixtures containing the same, as well as lower-boiling, components. Preferably, the higher-boiling hydrocarbons are $C_{3+}$ or $C_{4+}$ hydrocarbons. With respect to the lower-boiling components in the crude gas treated by the process, the gas can contain, for example, one or more of the following components:

He, $H_2$, CO, $N_2$, Ar, $CO_2$, $CH_4$, $C_2H_4$, $C_2H_6$.

The crude gas treated by the invention is generally at a pressure of 25 to 80 bar, preferably 35 to 50 bar, and a temperature of 0 to 45° C., preferably 15 to 35° C.

After partial condensation of the crude gas in a heat exchange means, the partially condensed crude gas is delivered to a separator. The separator generally operates at a pressure of about 25 to 80 bar, preferably 35 to 70 bar, and a temperature of −30 to −60° C., preferably −40 to −50° C. When the liquid fraction discharged from the separator is expanded as shown in the embodiment illustrated in FIG. 1, the liquid fraction is expanded to a pressure of 25 to 40 bar, preferably 32 to 38 bar. Similarly, when the gaseous fraction discharged from the separator is subjected to expansion as shown in FIG. 1, the gaseous fraction is expanded to a pressure of 25 to 60 bar, preferably 30 to 40 bar. Conversely, when the liquid fraction is subjected to compression as shown in the embodiment illustrated in FIG. 2, the liquid fraction is compressed to a pressure of 25 to 40 bar, preferably 32 to 38 bar.

The scrubbing column generally operates at a pressure of 25 to 60 bar, preferably 30 to 40 bar, and a temperature of −35° to −65° C., preferably −45° to −55° C. The scrubbing column may contain a number of theoretical plates, for example, 2 to 10 plates, preferably 3 to 6 plates.

The rectification column generally operates at a pressure of 25 to 40 bar, preferably 32 to 38 bar, and a temperature of −40° to 10° C., preferably −30° to 0° C. at the top of the rectification column. The rectification column can also contain a number of theoretical plates, e.g., 20 to 35 plates, preferably 25 to 32 plates.

In the process, the product stream containing essentially $C_{3+}$ or $C_{4+}$ hydrocarbons generally has a $C_{3+}$ or $C_{4+}$ hydrocarbon content of at least about 90%, preferably 98%. In addition, the fraction discharged from the bottom of the scrubbing column which is enriched in $C_{3+}$ or $C_{4+}$ hydrocarbons generally has a content of $C_{3+}$ or $C_{4+}$ hydrocarbons of at least about 30%, preferably 40%.

The process according to the invention can be used to recover either $C_{3+}$ or $C_{4+}$ hydrocarbons from a crude feed gas stream containing such hydrocarbons as well as lower-boiling components. Selection of the type of recovery, i.e., either $C_{3+}$ hydrocarbons or $C_{4+}$ hydrocarbons, is performed by selecting the relative operating parameters of the process from within the general ranges described herein. Determination of the respective operating parameters to be used with either type of recovery can be performed by one of ordinary skill in the art without having to resort to excessive or undue experimentation, based on the operating parameters described herein.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
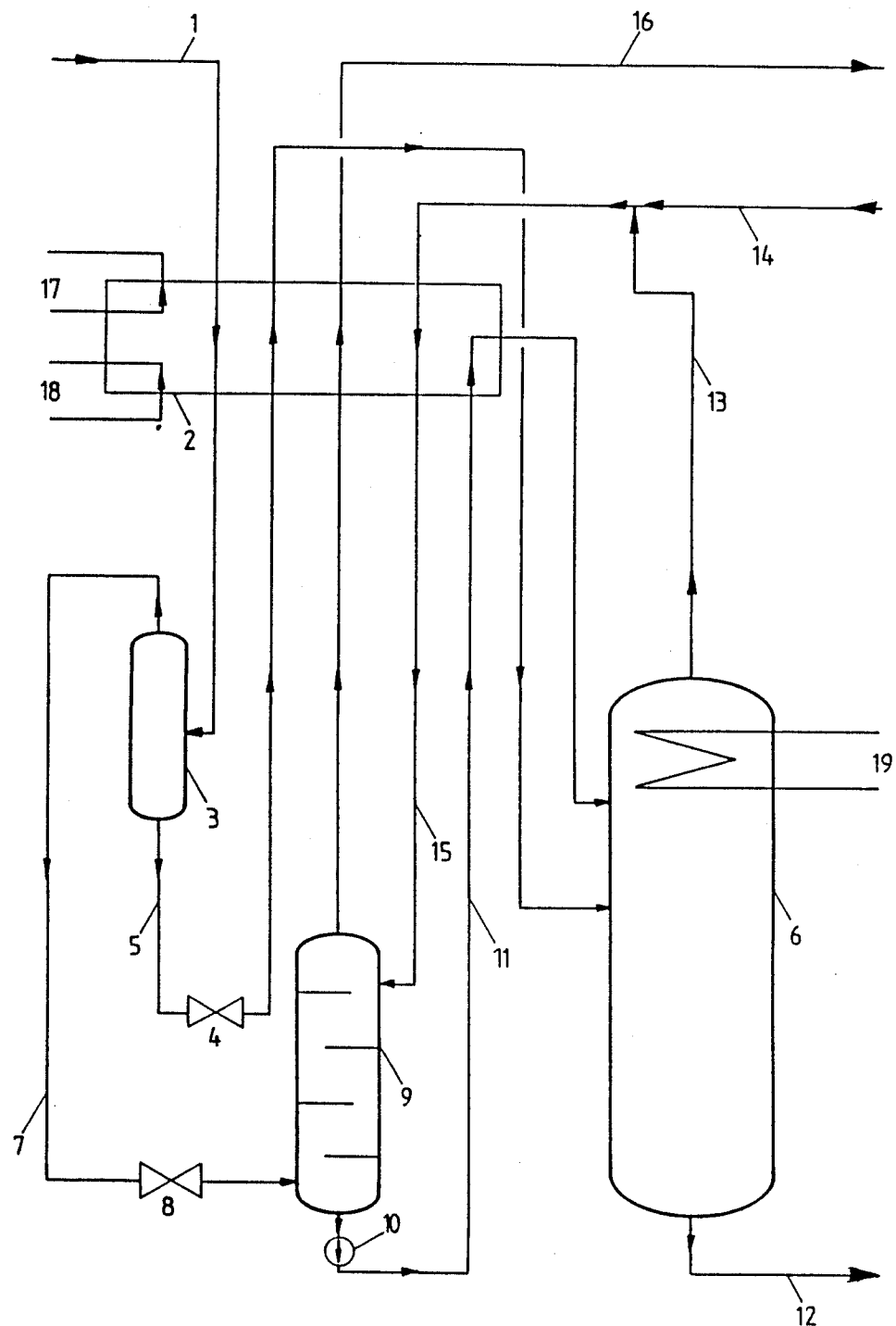
FIG. 1 illustrates a first embodiment of the process according to the invention wherein the pressure of the crude gas lies above the operating pressure of the rectifying column.

In the embodiment illustrated in FIG. 1, the gaseous stream to be fractionated, being under elevated pressure, is introduced via conduit 1 into a heat exchanger 2 wherein it is cooled to such an extent that a major portion of the hydrocarbons to be separated, i.e., $C_{3+}$ or $C_{4+}$ hydrocarbons, is condensed. In separator 3, the partially condensed gaseous stream is subjected to phase separation. The liquid fraction is withdrawn via a conduit 5, expanded by means of valve 4, and partially vaporized in heat exchanger 2 before being introduced into rectifying column 6. In the rectifying column 6, a final separation of lower-boiling components takes place, and a high purity $C_{3+}$ or $C_{4+}$ product fraction is withdrawn from the bottom of the column by way of conduit 12. This product fraction can be passed on to further separation (not illustrated). The residual gas fraction removed via conduit 13 from the head of the rectifying column 6 is mixed with a liquid stream of heavy hydrocarbons, such as $C_{3+}$, $C_{4+}$ or $C_{5+}$ hydrocarbons fed by means of conduit 14. This mixture stream is conducted in conduit 15 through heat exchanger 2, cooled therein, and introduced at the head of the scrubbing column 9. At the lower end of the scrubbing column 9, the gaseous fraction discharged from separator 3 is introduced via conduit 7 after expansion in valve 8. On account of the scrubbing out of higher-boiling components from the gaseous fraction, taking place in the scrubbing column, it is possible to remove overhead a gaseous stream depleted in higher-boiling components. This gaseous stream can leave the system via conduit 16 after being warmed in heat exchanger 2.

The liquid fraction, enriched in higher-boiling hydrocarbons, obtained from the bottom of the scrubbing column is compressed by means of pump 10 to the operating pressure of the rectifying column 6 and introduced, via conduit 11, after heating up in heat exchanger 2, into the rectifying column 6 where the final separation is performed together with the stream from conduit 5. By means of the heat exchanger 19 arranged at the head of rectifying column 6, higher-boiling hydrocarbons are condensed out of the rising gaseous fraction. In conduits 17 and 18, process streams of a refrigerating cycle, to be heated up, are conducted in order to enhance the process.

The embodiment shown herein is recommend in case of inlet pressures of the crude gas lying at least about 3 bar above the pressure of the product gas ambient in conduit 16. For FIG. 1, the pressure in conduit 16 can range maximally at about 36 bar so that the crude gas pressure can be 39 bar and higher. To provide pressures greater than 36 bar in line 16, the residual gas stream 13 of the rectification column 6 has to be compressed to the scrubbing pressure (this embodiment is not illustrated).

In the embodiment shown in FIG. 1, a yield of 91.6% of C3 hydrocarbons is achieved, considering the parameters and data set out below. In contrast thereto, the conventional process of DOS 3,511,636 shows, under identical conditions, a yield of merely 76%.

The operating parameters for the embodiment of FIG. 1 are presented in Table I.

TABLE I

| Conduit | (Data in Mol-%) | | | | | |
|---|---|---|---|---|---|---|
| | 1 | 11 | 12 | 13 | 14 | 16 |
| N2 | 1.5 | 0.2 | — | 0.4 | — | 1.6 |
| CO2 | 2.4 | 3.0 | — | 4.7 | — | 2.5 |
| CH4 | 82.1 | 35.8 | — | 64.7 | — | 87.5 |
| C2 | 7.7 | 21.7 | 0.5 | 29.9 | — | 8.1 |
| C3 | 3.8 | 19.1 | 51.5 | 0.3 | — | 0.3 |
| C4 | 2.0 | 5.3 | 29.0 | — | 0.8 | — |
| C5+ | 0.5 | 14.9 | 19.0 | — | 99.2 | — |
| Conduit/Container | | 3 | 6 | 9 | | 14 |
| Operating Pressure (bar) p: | | 48.6 | 36.0 | 35.5 | | 40.0 |
| Crude Gas Stream: | | Temperature = 20° C. | | | | |
| | | Pressure = 49 bar | | | | |

The embodiment of FIG. 1 is preferably used for crude gas pressures of 40 to 80 bar, especially 40 to 70 bar.

Figure 2:
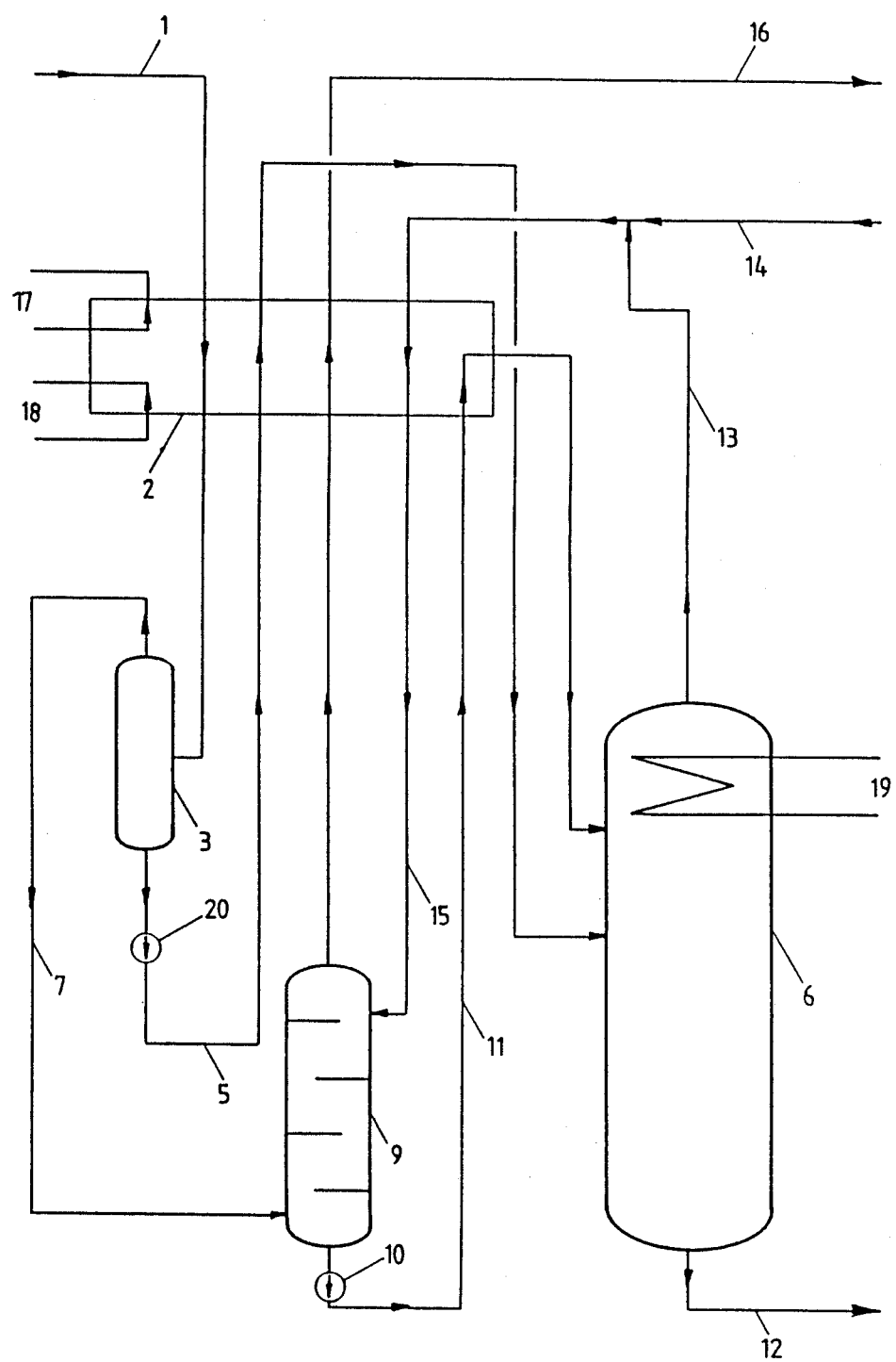
FIG. 2 illustrates a modified form of the process of the invention wherein the pressure of the crude gas and the operating pressure of the rectifying column are approximately the same.

The embodiment according to this invention as shown in FIG. 2 differs from that of FIG. 1 with regard to the inlet pressure of the crude gas. Instead of expansion of the gaseous and liquid fractions 7 and 5 of separator 3 by means of valves 4 and 8, compression of the liquid fraction 5 by means of pump 20 is performed. In this variation of the process, approximately identical operating pressures prevail in separator 3, scrubbing column 9, and rectifying column 6. This embodiment, in case of applications in low pressure range, is advantageous for securing a maximally high final pressure of the product gas.

By means of the process illustrated in FIG. 2, a yield of 95.6% C3 is obtained for a gaseous stream as specified hereinbelow. Without utilizing the process according to this invention, the yield attained was 90%.

The operating parameters for the embodiment of FIG. 2 are set forth in Table II.

TABLE II

| Conduit | (Data in Mol %) | | | | | |
|---|---|---|---|---|---|---|
| | 1 | 11 | 12 | 13 | 14 | 16 |
| H2 | 40.9 | 0.8 | — | 1.8 | — | 45.0 |
| N2 | 9.6 | 0.8 | — | 1.7 | — | 10.6 |
| CO | 2.0 | 0.2 | — | 0.4 | — | 2.2 |
| CO2 | 14.0 | 36.7 | — | 59.8 | — | 15.4 |
| CH4 | 19.4 | 5.7 | — | 12.0 | — | 21.4 |
| C2 | 4.8 | 11.2 | 0.2 | 21.1 | — | 5.2 |
| C3 | 5.4 | 26.4 | 52.4 | 3.1 | — | 0.2 |
| C4 | 2.9 | 2.9 | 29.3 | — | 0.8 | — |
| C5+ | 1.0 | 15.3 | 18.1 | — | 99.2 | — |
| Conduit/Container | | 3 | 6 | 9 | | 14 |
| Operating Pressure (bar) p: | | 33.7 | 33.2 | 32.5 | | 36 |

TABLE II-continued

| | (Data in Mol %) | | | | |
|---|---|---|---|---|---|
| Conduit | 1 | 11 | 12 | 13 | 14 | 16 |
| Crude Gas Stream: | | Temperature = 20° C. | | | |
| | | Pressure = 34 bar | | | |

The embodiment of FIG. 2 is preferably employed when the crude gas pressure is 25 to 40 bar, especially 0 to 35 bar.

Figure 3:
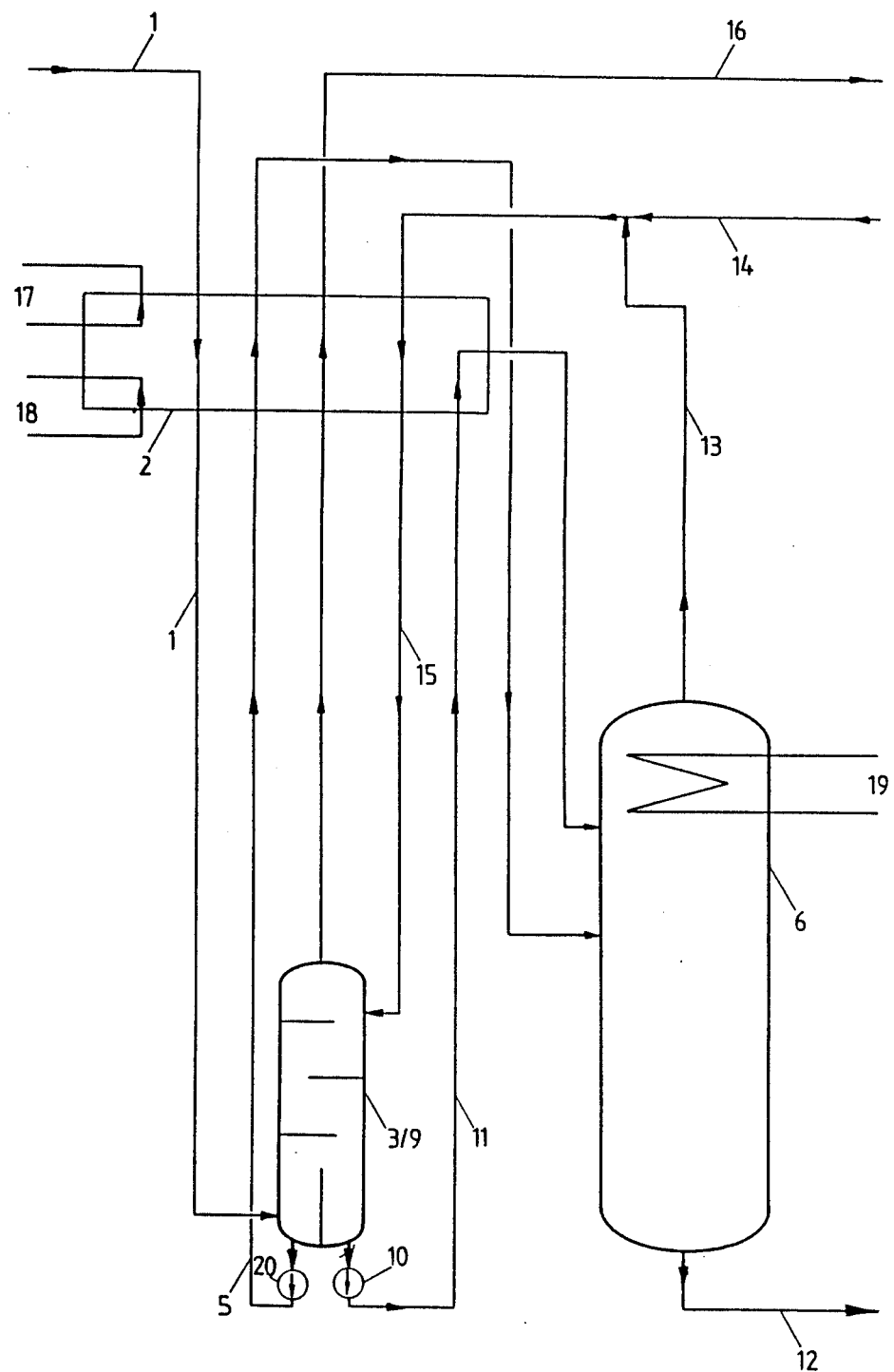
FIG. 3 illustrates a further embodiment of the process according to the invention wherein the separator and scrubbing column are integrated in one structural unit.

The embodiment of the process of this invention as shown in FIG. 3 represents a modification of the version of FIG. 2. Separator 3 and scrubbing column 9 are integrated into one structural unit 3/9 whereby the separator 3 can be eliminated. The structural unit 3/9 is of such a design that the bottom liquids of both separating steps are cooled and withdrawn separately whereas the gaseous head fraction from the partial condensation can be directly scrubbed, eliminating conduit 7.

The embodiment of FIG. 3 is preferably employed for the same crude gas pressure ranges as previously described for the embodiment of FIG. 2.

In case of crude gas pressures ranging far above the operating pressures of the scrubbing column and rectifying column, i.e., pressures higher than about 50 bar, it can be worthwhile to subject the gaseous fraction of the separation to engine expansion. In such a case, in FIG. 1, for example, an expansion machine would then be installed in conduit 7 in place of valve 8.

The preceding examples can be repeated with similar success by substituting the generically or specifically described reactants and/or operating conditions of this invention for those used in the preceding examples.

The entire texts of all applications, patents and publications cited above and of corresponding German application P 38 02 553.1 (the priority document), are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the separation of higher-boiling hydrocarbons from a crude gaseous stream container the latter and lower-boiling components, comprising:

cooling and partially condensing said crude gaseous stream, and separating the partially condensed gaseous stream into a liquid fraction and a gaseous fraction;

fractionating said liquid fraction by a rectification step into a produce stream container essentially higher-boiling hydrocarbons and into a residual gas stream containing lower-boiling components;

conducting said gaseous fraction separated after partial condensation to a scrubbing column wherein higher-boiling hydrocarbons are scrubbed out of said gaseous fraction using a scrubbing medium;

delivering a fraction enriched in higher-boiling hydrocarbons obtained from the bottom of said scrubbing column to said rectification step; and wherein said scrubbing medium is an admixture formed by adding a liquid stream of $C_{3+}$, $C_{4+}$ or $C_{5+}$ hydrocarbons to residual gas obtained in said rectification step, said residual gas being subjected to partial condensation prior to use of said admixture as a scrubbing medium.

2. A process according to claim 1, wherein said higher-boiling hydrocarbons are $C_{3+}$ hydrocarbons.

3. A process according to claim 1, wherein said higher-boiling hydrocarbons are $C_{4+}$ hydrocarbons.

4. A process according to claim 1, wherein a liquid stream of $C_{3+}$ hydrocarbons is added to said residual gas.

5. A process according to claim 1, wherein a liquid stream of $C_{4+}$ hydrocarbons is added to said residual gas.

6. A process according to claim 1, wherein a liquid stream of $C_{5+}$ hydrocarbons is added to said residual gas.

7. A process according to claim 3, wherein a liquid stream of $C_{4+}$ hydrocarbons is added to said residual gas.

8. A process according to claim 3, wherein a liquid stream of $C_{5+}$ hydrocarbons is added to said residual gas.

9. A process according to claim 1, wherein the liquid $C_{3+}$, $C_{4+}$ or $C_{5+}$ hydrocarbons added to the gaseous residual gas are obtained from a further fractionation of a product stream of said rectification step which contains $C_{3+}$ or $C_{4+}$ hydrocarbons.

10. A process according to claim 1, wherein said gaseous stream contains a high proportion of $CO_2$.

11. A process according to claim 1, further comprising removing a gaseous stream depleted in higher-boiling components from the head of said scrubbing column and wherein the pressure of said crude gaseous stream is at least 3 bar above the pressure of said gaseous stream depleted in higher-boiling components.

12. A process according to claim 1, wherein said liquid fraction is subjected to expansion prior to delivery to said rectification step and said gaseous fraction is subjected to expansion prior to delivery to said scrubbing column.

13. A process according to claim 1, wherein said liquid fraction is subjected to compression prior to delivery to said rectification step.

14. A process according to claim 13, wherein said gaseous fraction is delivered directly to the scrubbing column without passing through expansion means or compression means.

15. A process according to claim 1, wherein separation of the partially condensed gaseous stream into said liquid fraction and said gaseous fraction and scrubbing of said gaseous fraction are performed together in an integrated separator/scrubbing column.

16. A process according to claim 1, wherein the pressure of said crude gaseous stream is greater than the operating pressure of said rectification step.

17. A process according to claim 1, wherein the pressure of said crude gaseous stream is substantially the same as the operating pressure of said rectification step.

18. A process according to claim 16, wherein the pressure of said crude gas stream is about 50 bar and further comprising subjecting said gaseous fraction to engine expansion prior to delivery to said scrubbing column.

19. An apparatus for the separation of higher-boiling hydrocarbons from a gaseous stream containing higher-boiling hydrocarbons and lower-boiling components, comprising:

a scrubbing column, said scrubbing column having a first inlet means in a lower portion thereof for introduction of a gaseous fraction and a second inlet means, in an upper portion of the scrubbing column, for delivery of scrubbing medium, said scrubbing column also having a first outlet means in the upper portion thereof for removal of a residual gas stream and a second outlet means in the lower portion thereof for removal of loaded scrubbing medium;

first delivery means connected to said second outlet of said scrubbing column for removing loaded scrubbing medium from the scrubbing column and delivering same to a heat exchanger wherein loaded scrubbing medium is heated;

a rectification column, said rectification column comprising a first inlet means, in fluid communication with said first delivery means, for the introduction of heated, loaded scrubbing medium to said rectification column, a heat exchanger in an upper portion of said rectification column to condense higher-boiling hydrocarbons from a rising gaseous fraction, a product outlet means in a lower portion of said rectification column for removal of a product stream of higher-boiling hydrocarbons, and a gas outlet means in the head of said rectification column for the discharge of a residual gas fraction;

second delivery means, connected to said gas outlet of said rectification column, for delivering a residual gas fraction to a heat exchange means, wherein the residual gas fraction is subject to condensation, and subsequently delivering a condensed residual gas fraction to said second inlet means of said scrubbing column, wherein condensed residual gas fraction is employed as scrubbing medium; and admixture means in fluid communication with said second delivery means at a point upstream of said heat exchange means wherein a liquid stream of higher-boiling hydrocarbons is admixed with residual gas prior to condensation in said heat exchange means.

20. An apparatus according to claim 19, further comprising:

a separator located upstream of said scrubbing column, said separator comprising an inlet for introduction of partially condensed crude gas, a first outlet for removal of a gaseous fraction, said first outlet being in fluid communication with said first inlet means of said scrubbing column, and a second outlet for removal of a liquid fraction; and a third delivery means, connected to said second outlet of said separator, for delivering a liquid fraction to a heat exchange means, wherein the liquid fraction is heated, and subsequently delivering the heated liquid fraction to said rectification column.

21. An apparatus according to claim 20, wherein the introduction point of the heated liquid fraction to said rectification column is below the introduction point of the heated loaded scrubbing medium.

22. An apparatus according to claim 19, wherein said scrubbing column is a separator/scrubbing column integrated unit further comprising:

a dividing means located in the bottom portion thereof separating the bottom portion into two separate bottom portions, and a third outlet means in fluid communication with a first bottom portion for removal of a liquid fraction, said first inlet means being in communication with said first bottom portion of said separator/scrubbing column and delivering to said first bottom portion a partially condensed crude gas stream, and said second outlet means being in fluid communication with a second bottom portion of the separator/scrubbing column which receives loaded scrubbing medium; and said apparatus further comprising a third delivery means, connected with said third outlet means of said separator/scrubbing column, for delivering the liquid fraction to a heat exchange means, wherein the liquid fraction is heated, and subsequently delivering the heated liquid fraction to said rectification column.

23. An apparatus according to claim 22, wherein the introduction point of the heated liquid fraction to said rectification column is below the introduction point of the heated loaded scrubbing medium.

* * * * *